US012660991B2

(12) United States Patent
Yi et al.

(10) Patent No.: US 12,660,991 B2
(45) Date of Patent: Jun. 23, 2026

(54) ENDOSCOPE WIRE PULLING WHEEL, ENDOSCOPE HANDLE, AND ENDOSCOPE

(71) Applicant: GUANGZHOU RED PINE MEDICAL INSTRUMENT CO., LTD., Guangzhou (CN)

(72) Inventors: Feng Yi, Guangzhou (CN); Jing Li, Guangzhou (CN); Xiaofeng Tan, Guangzhou (CN)

(73) Assignee: GUANGZHOU RED PINE MEDICAL INSTRUMENT CO., LTD., Guangzhou (CN)

( * ) Notice: Subject to any disclaimer, the term of this patent is extended or adjusted under 35 U.S.C. 154(b) by 265 days.

(21) Appl. No.: 18/574,945

(22) PCT Filed: Dec. 2, 2022

(86) PCT No.: PCT/CN2022/136236
§ 371 (c)(1),
(2) Date: Dec. 28, 2023

(87) PCT Pub. No.: WO2023/103909
PCT Pub. Date: Jun. 15, 2023

(65) Prior Publication Data
US 2024/0315538 A1 Sep. 26, 2024

(30) Foreign Application Priority Data

Dec. 7, 2021 (CN) .......................... 202123060327.2

(51) Int. Cl.
*A61B 1/005* (2006.01)

(52) U.S. Cl.
CPC ............ *A61B 1/005* (2013.01); *A61B 1/0052* (2013.01)

(58) Field of Classification Search
CPC ... A61B 1/00066; A61B 1/005; A61B 1/0052; A61B 1/0057
See application file for complete search history.

(56) References Cited

U.S. PATENT DOCUMENTS 4,483,326 A 11/1984 Yamaka et al.
2002/0143238 A1* 10/2002 Hino ..................... A61B 1/0057
600/146

(Continued)

FOREIGN PATENT DOCUMENTS

CN 1575744 A 2/2005
CN 102711582 A 10/2012

(Continued)

OTHER PUBLICATIONS

Notice of Allowance (with English translation) received in corresponding Patent Application JP 2024-516534, dated Jun. 10, 2025, 4 pages.

(Continued)

*Primary Examiner* — Aaron B Fairchild
(74) *Attorney, Agent, or Firm* — Dority & Manning, PA

(57) ABSTRACT

Disclosed are an endoscope wire pulling wheel, an endoscope handle, and an endoscope. During a winding process, both ends of a pull wire are respectively distributed at two opposite sides of a winding part; then, the two ends of the pull wire are respectively correspondingly wound in the two winding grooves in opposite directions. Since the two wire winding grooves are provided with wire penetrating holes communicated with a cavity, after the pull wire is wound, the ends of the pull wire can penetrate through one wire penetrating hole to the cavity, and then penetrate through the other wire penetrating hole from the cavity; and the penetration is repeated such that the ends of the pull wire can be stably fixed on the winding part.

9 Claims, 4 Drawing Sheets

(56)  References Cited

U.S. PATENT DOCUMENTS

| | | | |
|---|---|---|---|
| 2012/0078054 A1* | 3/2012 | Ueno | ................... A61B 1/0057 |
| | | | 600/149 |
| 2012/0220832 A1 | 8/2012 | Nakade et al. | |
| 2021/0338049 A1 | 11/2021 | Christensen | |

FOREIGN PATENT DOCUMENTS

| | | | | |
|---|---|---|---|---|
| CN | 206007203 U | * | 3/2017 | ........... A61B 1/0052 |
| CN | 208541276 U | | 2/2019 | |
| CN | 210990437 U | | 7/2020 | |
| CN | 113576375 A | | 11/2021 | |
| CN | 216724501 U | | 6/2022 | |
| CN | 115153388 A | | 10/2022 | |
| EP | 4382022 A1 | | 6/2024 | |
| JP | S 6047503 U | | 4/1985 | |
| JP | H 0882749 A | | 3/1996 | |
| JP | 2002291686 A | | 10/2002 | |
| JP | 2005021629 A | | 1/2005 | |
| JP | 2011143029 A | | 7/2011 | |
| WO | WO2018029908 A1 | | 2/2018 | |
| WO | WO2019123814 A1 | | 6/2019 | |

OTHER PUBLICATIONS

European Search Report received in corresponding Application No. EP 22903331.1, dated Apr. 28, 2025, 10 pages.
Japanese Office Action (w/ English Translation) for corresponding Application No. JP2024516534, dated Jan. 21, 2025, 10 pages.
PCT International Search Report and Written Opinion (with English translations) for corresponding PCT Application No. PCT/CN2022/136236, mailed Feb. 24, 2023, 12 pages.

* cited by examiner

ENDOSCOPE WIRE PULLING WHEEL, ENDOSCOPE HANDLE, AND ENDOSCOPE

CROSS-REFERENCE TO RELATED APPLICATIONS

This application is an U.S. national phase application under 35 U.S.C. § 371 based upon international patent application PCT/CN2022/136236, filed on Dec. 2, 2022, which itself claims priority to Chinese patent application No. 202123060327.2, filed on Dec. 7, 2021. The contents of the above identified applications are hereby incorporated herein in their entireties by reference.

TECHNICAL FIELD

The present utility model relates to the field of medical device technologies, and in particular, to an endoscope wire draw wheel, an endoscope handle, and an endoscope.

BACKGROUND

In order to clearly and intuitively understand a location of a lesion and improve the accuracy of diagnosis of the lesion, endoscopes play a vital role in the procedure. A conventional endoscope includes a handle, an insertion tube, a bending section, a tip, a host, and the like. A knob apparatus is provided inside the handle, so as to control the bending section to bend in different directions, and define a bending angle of the bending section. The knob apparatus includes a traction wire, a wire draw wheel, an angle control knob, and the like. The traction wire is usually bonded to the wire draw wheel by glue or welded to the wire draw wheel. As a result, the traction wire is easy to fall off and has a higher fraction defective, and the fixing method is difficult and the assembly efficiency is low.

SUMMARY

Accordingly, it is necessary to provide an endoscope wire draw wheel, an endoscope handle, and an endoscope, so as to effectively and reliably fix a traction wire, and improve a wire fixing rate. In addition, the wire fixing operation is convenient and the assembly efficiency is improved.

An endoscope wire draw wheel includes a mounting portion and a wire winding portion. The mounting portion is configured to be rotatably mounted in a housing. The wire winding portion is provided on the mounting portion. An outer wall of the wire winding portion is provided with two wire winding grooves spaced apart along an axial direction of the wire winding portion. Each of the wire winding grooves is arranged extending along a circumferential direction of the wire winding portion. Groove walls of the two wire winding grooves are provided with wire leading holes. A cavity is provided in the wire winding portion. Each of the wire leading holes is in communication with the cavity.

In the aforementioned endoscope wire draw wheel, during a wire winding process, both ends of the traction wire are distributed on opposite sides of the wire winding portion, respectively, then, the both ends of the traction wire are correspondingly wound in two wire winding grooves in opposite directions, respectively. As such, when the wire winding portion rotates in one direction, one end of the traction wire is in a release state, and the other end of the traction wire is in a winding state, so as to control the bending section to bend in different directions. The two wire winding grooves are provided with wire leading holes in communication with the cavity, therefore, after the traction wire is wound, a wire end of the traction wire can be led to the cavity through one wire leading hole and then passes through the other wire leading hole from the cavity. Repeating in this way, the wire end of the traction wire can be steadily fixed on the wire winding portion. Compared with a conventional bonding or welding manner, this design can implement reliable fixing of the traction wire by improving a structure on the wire winding portion, without adding additional fixing parts or external equipment, which helps to improve a wire fixing efficiency. In addition, the wire fixing operation is convenient and the assembly efficiency is improved.

In one of the embodiments, groove walls of each of the wire winding grooves are provided with at least two wire leading holes that are spaced apart along the circumferential direction of the wire winding portion.

In one of the embodiments, an inner wall of the cavity is provided with at least two grooves spaced apart along the circumferential direction of the wire winding portion. Each of the grooves is arranged extending along the axial direction of the wire winding portion, and the two grooved are in communication with the two wire winding grooves to form the wire leading holes.

In one of the embodiments, a wire winding block is formed between adjacent two grooves, a traction wire is wound around the wire winding block.

In one of the embodiments, the mounting portion or the wire winding portion is provided with a limit protrusion configured to be engaged with a limit structure in the housing, so as to limit a rotation range of the mounting portion.

In one of the embodiments, the mounting portion or the wire winding portion is provided with a positioning hole configured to be engaged with a positioning structure in the housing to prevent the mounting portion from rotating. In one of the embodiments, the mounting portion is provided with a first buckle portion configured to be engaged with a second buckle portion of an angle control knob.

In one of the embodiments, the wire winding portion is provided with three convex rings spaced apart along the axial direction of the wire winding portion, and the wire winding groove is formed between adjacent two convex rings.

An endoscope handle includes a housing, a traction wire and the endoscope wire draw wheel according to any one of the aforementioned embodiments. The wire winding portion is rotatably mounted in the housing via the mounting portion. Both ends of the traction wire are correspondingly wound around the two wire winding grooves, respectively, and both ends of the traction wire extend through at least two of the wire leading holes, respectively.

In the aforementioned endoscope handle adopting the above endoscope wire draw wheel, during the wire winding process, both ends of the traction wire are distributed on opposite sides of the wire winding portion, respectively, then, both ends of the traction wire are correspondingly wound in two wire winding grooves in opposite directions, respectively. As such, when the wire winding portion rotates in one direction, one end of the traction wire is in a release state, and the other end of the traction wire is in a winding state, so as to control the bending portion to bend in different directions. The two wire winding grooves are provided with wire leading holes in communication with the cavity, therefore, after the traction wire is wound, a wire end of the traction wire can be led to the cavity through one wire leading hole and then passes through the other wire leading hole from the cavity. Repeating in this way, the wire end of the traction wire can be steadily fixed on the wire winding portion. Compared with a conventional bonding or welding manner, this design can implement reliable fixing of the traction wire by improving a structure on the wire winding portion, without adding additional fixing parts or external equipment, which helps to improve a wire fixing efficiency. In addition, the wire fixing operation is convenient and the assembly efficiency is improved.

An endoscope includes the aforementioned endoscope handle.

In the aforementioned endoscope adopting the aforementioned wire draw wheel, during a wire winding process, both ends of the traction wire are distributed on opposite sides of the wire winding portion, respectively, then, both ends of the traction wire are correspondingly wound in two wire winding grooves in opposite directions, respectively. As such, when the wire winding portion rotates in one direction, one end of the traction wire is in a release state, and the other end of the traction wire is in a winding state, so as to control the bending portion to bend in different directions. The two wire winding grooves are provided with wire leading holes in communication with the cavity, therefore, after the traction wire is wound, a wire end of the traction wire can be led to the cavity through one wire leading hole and then passes through the other wire leading hole from the cavity. Repeating in this way, the wire end of the traction wire can be steadily fixed on the wire winding portion. Compared with a conventional bonding or welding manner, this design can implement reliable fixing of the traction wire by improving a structure on the wire winding portion, without adding additional fixing parts or external equipment, which helps to improve a wire fixing efficiency. In addition, the wire fixing operation is convenient and the assembly efficiency is improved.

BRIEF DESCRIPTION OF THE DRAWINGS

The accompanying drawings that constitute a part of the present utility model are used to provide a further understanding of the present utility model. The exemplary embodiments of the present utility model and descriptions thereof are used to explain the present utility model, and do not constitute an undue limitation on the present utility model.

To describe the technical solutions in the embodiments of the present utility model more clearly, the following briefly describes the accompanying drawings required for describing the embodiments. Apparently, the accompanying drawings in the following description show merely some embodiments of the present utility model, and a person of ordinary skill in the art may still derive other drawings from these accompanying drawings without creative efforts.

100. wire draw wheel; 110. mounting portion; 111. first buckle portion; 112. abutting protrusion; 120. wire winding portion; 121. wire winding groove; 122. wire leading hole;

123. cavity; 124. groove; 1241. wire winding block; 125. convex ring; 1251. limit protrusion; 1252. positioning hole.

DETAILED DESCRIPTION OF THE EMBODIMENTS

To make the foregoing objects, features, and advantages of the present utility model more obvious and easy to understand, the following describes a specific implementation manner of the present utility model in detail with reference to the accompanying drawings. Many specific details are described in the following description to facilitate full understanding of the present utility model. However, the present utility model can be implemented in many different manners from those described herein. A person skilled in the art may make similar improvements without departing from the connotation of the present utility model. Therefore, the present utility model is not limited to the specific embodiments disclosed below.

Figure 1:
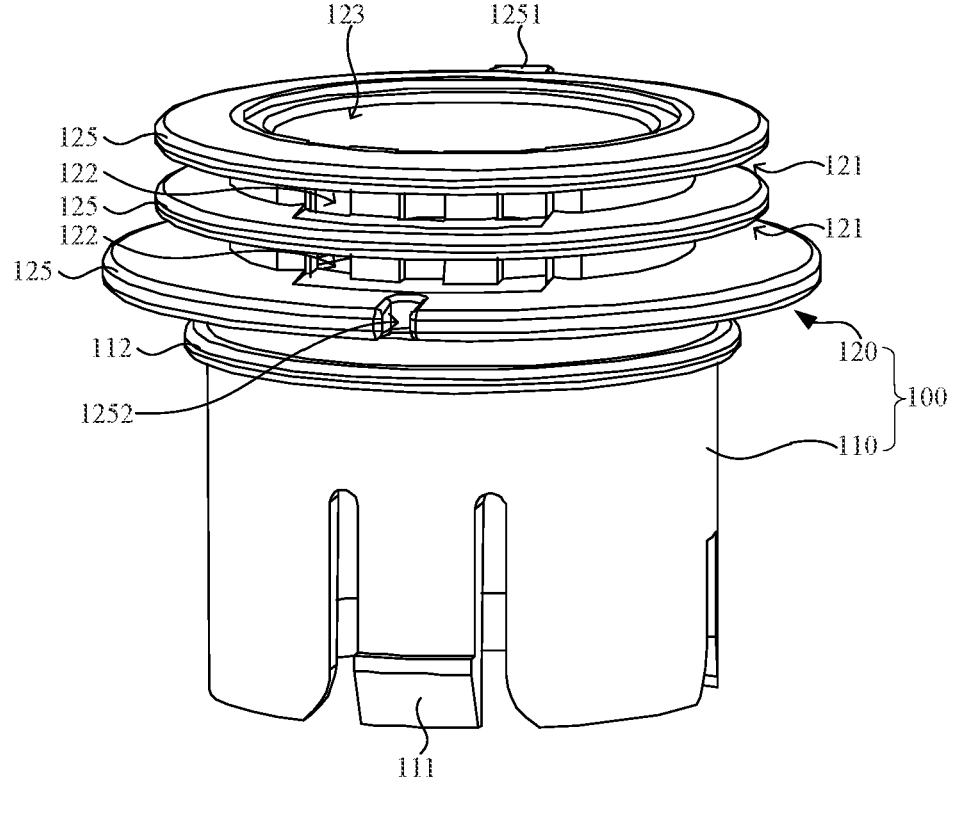
FIG. 1 is a structural view of an endoscope wire draw wheel according to an embodiment in a perspective view.
Figure 3:
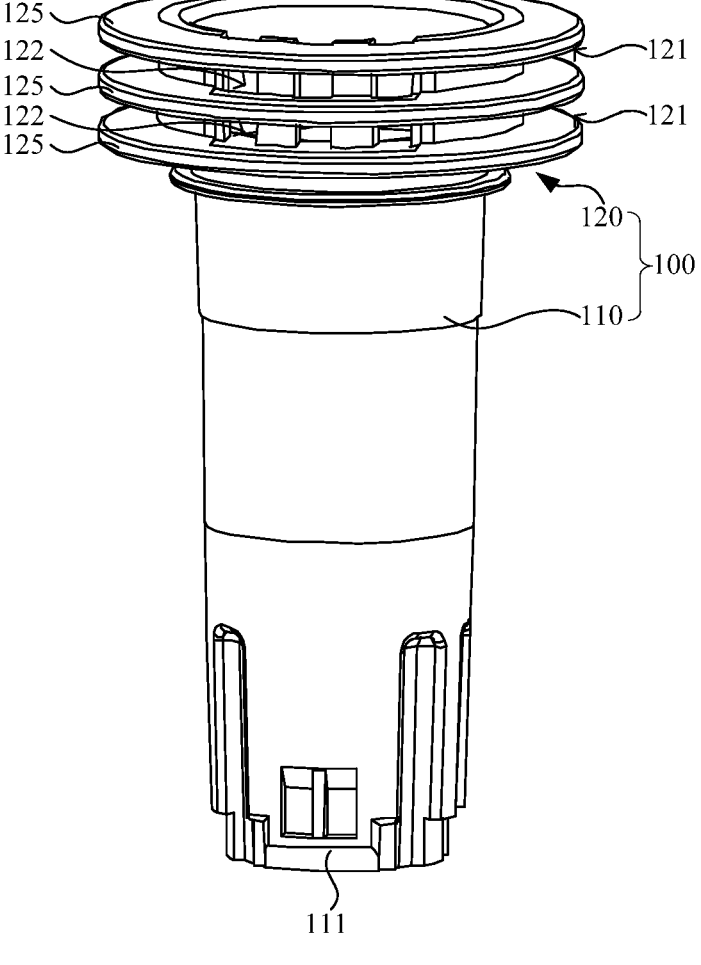
FIG. 3 is a structural view of an endoscope wire draw wheel according to another embodiment in a perspective view.

In an embodiment, referring to FIG. 1 and FIG. 3, an endoscope wire draw wheel 100 is provided, which includes a mounting portion 110 and a wire winding portion 120. The mounting portion 110 is configured to be rotatably mounted in a housing. The wire winding portion 120 is provided on the mounting portion 110, and two wire winding grooves 121 are provided on an outer wall of the wire winding portion 120. The two wire winding grooves 121 are spaced apart along an axial direction of the wire winding portion 120. Each of the wire winding grooves 121 is arranged extending along a circumferential direction of the wire winding portion 120. Groove walls of the two wire winding grooves 121 are provided with wire leading holes 122, and a cavity 123 is provided in the wire winding portion 120. Each of the wire leading holes 122 is in communication with the cavity 123.

In the aforementioned endoscope wire draw wheel 100, during a wire winding process, both ends of the traction wire are distributed on opposite sides of the wire winding portion 120, respectively, then, both ends of the traction wire are correspondingly wound in two wire winding grooves 121 in opposite directions, respectively. As such, when the wire winding portion 120 rotates in one direction, one end of the traction wire is in a release state, and the other end of the traction wire is in a winding state, so as to control a bending portion to bend in different directions. The two wire winding grooves 121 are provided with wire leading holes 122 in communication with the cavity 123, therefore, after the traction wire is wound, a wire end of the traction wire can be led to the cavity 123 through one wire leading hole 122 and then passes through the other wire leading hole 122 from the cavity 123. Repeating in this way, the wire end of the traction wire can be steadily fixed on the wire winding portion 120. Compared with a conventional bonding or welding manner, this design can implement reliable fixing of the traction wire by improving the structure on the wire winding portion 120, without adding additional fixing parts or external equipment, which helps to improve a wire fixing efficiency. In addition, the wire fixing operation is convenient and the assembly efficiency is improved.

It should be noted that each of the wire winding grooves 121 may have one, two, three, or more wire leading holes 122. When each of the wire winding grooves 121 is provided with two or more wire leading holes 122, there are a plurality of manners in which the wire end of the traction wire is led through the wire leading holes 122. For this reason, the embodiment is not specifically limited to this, as long as the traction wire is led through the wire leading holes 122 and can be stably fixed.

Optionally, a connection manner between the wire winding portion 120 and the mounting portion 110 may be but not limited to a bolt connection, a threaded socket, a clamping, a riveting, a welding, a bonding, an integrated molding manner, or the like. The integrated molding manner is an injection molding manner, a 3D printing manner, or the like.

Figure 2:
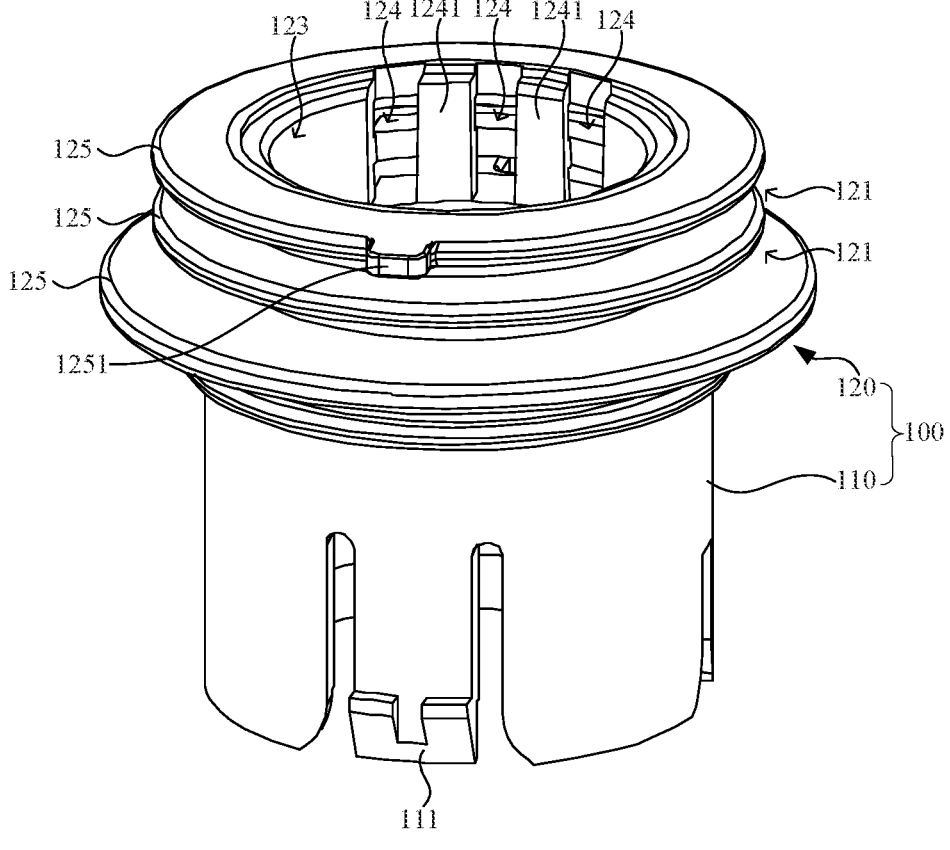
FIG. 2 is a structural view of the endoscope wire draw wheel according to an embodiment in another perspective view.

Further, referring to FIGS. 1 to 3, grooves wall of each of the wire winding grooves 121 are provided with at least two wire leading holes 120 that are spaced apart along the circumferential direction of the wire winding portion 120. In this embodiment, by increasing the number of the wire leading holes 122 increases, the leading manners of the traction wire increases, which not only strengths of binding between the traction wire and the wire winding portion 120 is improved, but also provides a plurality of leading manners for the operator to choose, so that the wire fixing operation is more convenient. For example, the wire end of the traction wire can be led between the wire leading holes 122 in the same wire winding groove 121, or the wire end of the traction wire can be led through between the wire leading holes 122 of adjacent two wire winding grooves 121.

Figure 4:
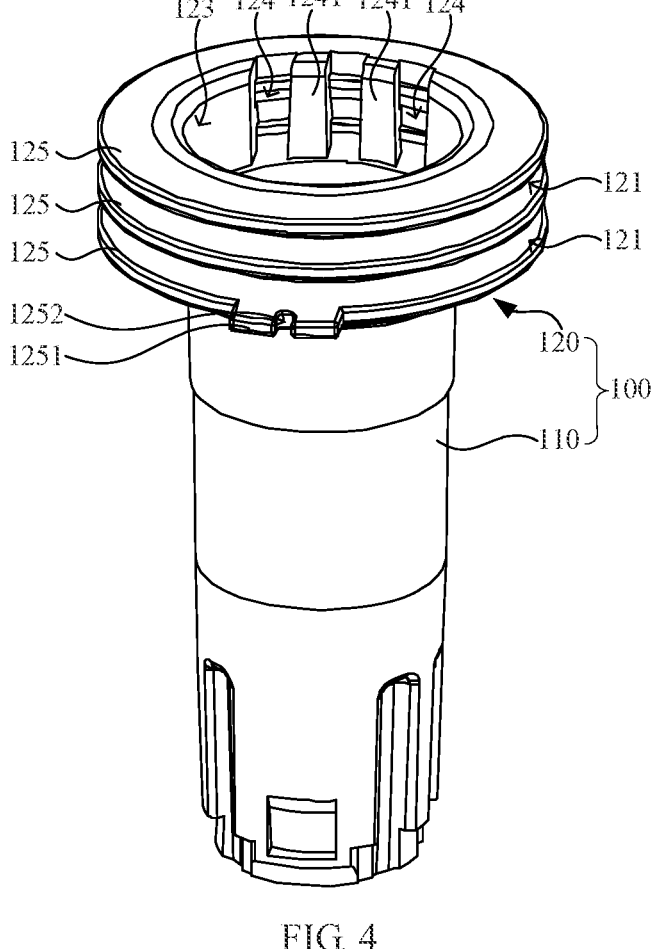
FIG. 4 is a structural view of the endoscope wire draw wheel according to another embodiment in another perspective view.

Further, referring to FIG. 2 and FIG. 4, at least two grooves 124 are provided on an inner wall of the cavity 123. The at least two grooves 124 are spaced apart along the circumferential direction of the wire winding portion 120, and each of the grooves 124 is arranged extending along the axial direction of the wire winding portion 120, and the two grooves 124 are in communication with the two wire winding grooves 121 to form the wire leading holes 122. It can be learned that the traction wire wound between the wire leading holes 122 in the two wire winding grooves 121 are located in the groove 124, and does not enter the cavity 123, so as to avoid affecting the mounting of the endoscope wire draw wheel 100.

In an embodiment, referring to FIG. 2 and FIG. 4, a wire winding block 1241 is formed between adjacent two grooves 124, and a traction wire is wound around the wire winding block 1241, so as to provide a wire winding support for the traction wire, thereby ensuring that the wire is fixed more firmly.

In an embodiment, referring to FIG. 2 and FIG. 4, a limit protrusion 1251 is provided on the mounting portion 110 or the wire winding portion 120. The limit protrusion 1251 is configured to be engaged with a limit structure in the housing to limit a rotation range of the mounting portion 110. It can be learned that when the endoscope wire draw wheel 100 rotates, the limit protrusion 1251 can be engaged with the limit structure in the housing, so that the endoscope wire draw wheel 100 cannot continue to rotate. In this way, a rotation range of the endoscope wire draw wheel 100 can be effectively limited, thus avoiding the traction wire from being broken due to excessive rotation, so as to ensure safe use of the endoscope.

In an embodiment, referring to FIG. 2 and FIG. 4, a positioning hole 1252 is provided on the mounting portion 110 or the wire winding portion 120. The positioning hole 1252 is configured to be engaged with the positioning structure in the housing to prevent the mounting portion 110 from rotating. Since the endoscope wire draw wheel 100 is in a freely rotatable state, the mounting portion 110 will rotate leftward and rightward during the wire winding process, thereby increasing operating difficulty of the wire winding. Therefore, in this embodiment, the positioning hole 1252 is provided, and during the wire winding process, the positioning hole 1252 is engaged with the positioning structure in the housing. Then a fastener is inserted into the positioning hole 1252 and the positioning structure, so as to limit the rotation of the mounting portion 110 and implement temporary fixing. When winding is complete, the fastener can be removed from the positioning hole 1252. The fastener may be but is not limited to a pin or the like.

It should be noted that the positioning hole 1252 may have a hole-like structure such as a semicircle hole, a semi-square hole, and a semi-elliptic hole.

In an embodiment, referring to FIG. 2 and FIG. 3, a first buckle portion 111 is provided on the mounting portion 110. The first buckle portion 111 is configured to be engaged with a second buckle portion of an angle control knob. In this way, the mounting portion 110 is stably connected to the angle control knob through the engagement of the first buckle portion 111 and the second buckle portion.

Optionally, the first buckle portion 111 is a buckle slot, and the second buckle portion is a buckle protrusion. Alternatively, the first buckle portion 111 is a buckle protrusion, and the second buckle portion is a buckle slot.

In an embodiment, referring to FIG. 1 and FIG. 3, three convex rings 125 are provided on the wire winding portion 120. The three convex rings 125 are spaced apart along an axial direction of the wire winding portion 120, and the wire winding groove 121 is formed between adjacent two convex rings 125. In this way, the wire winding grooves 121 are effectively separated by the convex rings 125, and an interconnection of wires can be effectively prevented.

In an embodiment, referring to FIG. 1, an endoscope handle is provided, which includes a housing, a traction wire, and an endoscope wire draw wheel 100 in the aforementioned embodiments. The wire winding portion 120 is rotatably mounted in the housing via the mounting portion 110. Both ends of the traction wire are wound in the two wire winding grooves 121, respectively, and both ends of the traction wire are disposed in at least two wire leading holes 122, respectively.

In the aforementioned endoscope handle adopting the above endoscope wire draw wheel 100, during a wire winding process, both ends of the traction wire are distributed on opposite sides of the wire winding portion 120, respectively, then, the two ends of the traction wire are correspondingly wound in two wire winding groove 121 in opposite directions, respectively. As such, when the wire winding portion 120 rotates in one direction, one end of the traction wire is in a release state, and the other end of the traction wire is in a winding state, so as to control the bending portion to bend in different directions. The two wire winding grooves 121 are provided with wire leading holes 122 in communication with the cavity 123, therefore, after the traction wire is wound, a wire end of the traction wire can be led to the cavity 123 through one wire leading hole 122 and then passes through the other wire leading hole 122 from the cavity 123. Repeating in this way, the wire end of the traction wire can be steadily fixed on the wire winding portion 120. Compared with a conventional bonding or welding manner, this design can implement reliable fixing of the traction wire by improving a structure on the wire winding portion 120, without adding additional fixing parts or external equipment, which helps to improve a wire fixing efficiency. In addition, the wire fixing operation is convenient and the assembly efficiency is improved.

In an embodiment, referring to FIG. 1, an endoscope is provided, which includes an endoscope handle in the aforementioned embodiments.

In the aforementioned endoscope adopting the above endoscope handle, during a wire winding process, both ends of the traction wire are distributed on opposite sides of the wire winding portion 120, respectively, then, the both ends of the traction wire are correspondingly wound in two wire winding groove 121 in opposite directions, respectively. As such, when the wire winding portion 120 rotates in one direction, one end of the traction wire is in a release state, and the other end of the traction wire is in a winding state, so as to control the bending portion to bend in different directions. The two wire winding grooves 121 are provided with wire leading holes 122 in communication with the cavity 123, therefore, after the traction wire is wound, a wire end of the traction wire can be led to the cavity 123 through one wire leading hole 122 and then passes through the other wire leading hole 122 from the cavity 123. Repeating in this way, the wire end of the traction wire can be steadily fixed on the wire winding portion 120. Compared with a conventional bonding or welding manner, this design can implement reliable fixing of the traction wire by improving a structure on the wire winding portion 120, without adding additional fixing parts or external equipment, which helps to improve a wire fixing efficiency. In addition, the wire fixing operation is convenient and the assembly efficiency is improved.

The technical features of the aforementioned embodiments may be combined arbitrarily. To simplify the description, not all the possible combinations of the technical features in the aforementioned embodiments are described. However, all of the combinations of these technical features should be considered as within the scope of the present disclosure, as long as such combinations do not contradict with each other.

The detailed embodiments described herein are only for the purpose of illustrating the present utility model, and are not intended to limit the scope of the present utility model in any way. It would be understand by a person skilled in the art that various changes and modifications can be made to the embodiments described herein without departing from the scope and spirit of the present utility model. Therefore, the protection scope of the present utility model should be defined by the following claims.

In the description of the present utility model, it should be understood that the orientation or location relationship indicated by terms such as "center", "longitudinal", "horizontal", "length", "width", "thickness", "upper", "lower", "front", "back", "left", "right", "vertical", "horizontal", "top", "bottom", "inside", "outside", "clockwise", "counterclockwise", "axial", "radial", "circumferential" is based on what is shown in the accompanying drawings, and is merely intended to facilitate and simplify the description of the present utility model, and is not intended to indicate or imply that the pointed device or element must have a specific orientation, or be constructed or operated in a specific orientation, and therefore, this is not to be understood as a limitation on the present utility model.

In addition, the terms "first" and "second" are only used for descriptive purposes, and should not be construed as indicating or implying relative importance or implying the number of indicated technical features. Thus, a feature delimited with "first" or "second" may expressly or implicitly include at least one of that feature. In the description of the present utility model, "plurality" means at least two, for example, two, three, or the like, unless otherwise specifically limited.

In the present utility model, the terms "mount". "interconnect", "connect", and "fix" are understood in a broad sense unless otherwise specified and limited. For example, the term may mean a fixed connection, may mean a detachable connection, or may mean integrated into one; or the term may mean a mechanical connection, or may mean an electrical connection: or the term may mean directly connected, or may mean indirectly connected by using an intermediate medium, or may mean connected between two elements, or an interaction relationship between the two elements, unless otherwise specifically limited. A person of ordinary skill in the art may understand a specific meaning of the aforementioned terms in the present utility model according to a specific situation.

In the present utility model, unless otherwise specified and limited, the first feature is "on" or "under" the second feature may mean the first feature is in direct contact with the second feature, or the first feature is in indirect contact with the second feature by using an intermediate medium. Also, the first feature is "above", "over" and "on" the second feature may mean that the first feature is directly above or obliquely above the second feature, or simply means that the first feature has a higher level than the second feature. The first feature being "below", "beneath" and "under" the second feature may mean that the first feature is directly or obliquely below the second feature, or simply means that the first feature has a lower level than the second feature.

It should be noted that when an element is referred to as being "fixed to" or "disposed on" another element, it can be directly on the other element or an intervening element may also be present. When an element is considered to be "connected to" another element, it can be directly connected to another element or indirectly connected to another element with a mediating element. The terms "vertical", "horizontal", "upper", "lower", "left", "right" and similar expressions used herein are for the purpose of illustration only and do not represent the only embodiment.

What is claimed is:

1. An endoscope wire draw wheel, comprising:
   a mounting portion configured to be rotatably mounted in a housing; and
   a wire winding portion provided on the mounting portion; wherein:
     an outer wall of the wire winding portion is provided with two wire winding grooves spaced apart along an axial direction of the wire winding portion;
     each of the wire winding grooves is arranged extending along a circumferential direction of the wire winding portion;
     groove walls of the two wire winding grooves are provided with wire leading holes;
     a cavity is provided in the wire winding portion; and
     each of the wire leading holes is in communication with the cavity; and
   groove walls of each wire winding groove are provided with at least two of the wire leading holes that are spaced apart along the circumferential direction of the wire winding portion.

2. The endoscope wire draw wheel according to claim 1, wherein an inner wall of the cavity is provided with at least two grooves spaced apart along the circumferential direction of the wire winding portion, and each of the grooves is arranged extending along the axial direction of the wire winding portion, and the wire leading holes communicate between the two grooves and the wire forming grooves.

3. The endoscope wire draw wheel according to claim 2, wherein a wire winding block is formed between adjacent two grooves, a traction wire is wound around the wire winding block.

4. The endoscope wire draw wheel according to claim 1, wherein the mounting portion or the wire winding portion is provided with a limit protrusion configured to be engaged with a limit structure in the housing, so as to limit a rotation range of the mounting portion.

5. The endoscope wire draw wheel according to claim 1, wherein the mounting portion or the wire winding portion is provided with a positioning hole configured to be engaged with a positioning structure in the housing to prevent the mounting portion from rotating.

6. The endoscope wire draw wheel according to claim 1, wherein the mounting portion is provided with a first buckle portion configured to be engaged with a second buckle portion of an angle control knob.

7. The endoscope wire draw wheel according to claim 1, wherein the wire winding portion is provided with three convex rings spaced apart along the axial direction of the wire winding portion, and each wire winding groove is formed between different pairs of adjacent two convex rings of the three convex rings.

8. An endoscope handle, comprising a housing, a traction wire, and the endoscope wire draw wheel according to claim 1, wherein the wire winding portion is rotatably mounted in the housing via the mounting portion, both ends of the traction wire are correspondingly wound around the two wire winding grooves, respectively, and both ends of the traction wire extend through at least two of the wire leading holes, respectively.

9. An endoscope, comprising the endoscope handle according to claim 8.

* * * * *